United States Patent [19]

Elslager et al.

[11] Patent Number: 4,505,925
[45] Date of Patent: Mar. 19, 1985

[54] N,N-DIETHYL-5-METHYL-2H-1-BENZOTHI-OPYRANO-4,3,2-CD-INDAZOLE-2-ETHANA-MINE COMPOSITIONS AND METHODS FOR THEIR USE

[75] Inventors: Edward F. Elslager; Leslie M. Werbel, both of Ann Arbor, Mich.

[73] Assignee: Warner-Lambert Company, Morris Plains, N.J.

[21] Appl. No.: 496,612

[22] Filed: May 20, 1983

[51] Int. Cl.³ .............................................. A61K 31/415
[52] U.S. Cl. .................................................. 514/405
[58] Field of Search ........................ 424/273 N, 273 P

[56] References Cited
U.S. PATENT DOCUMENTS
3,505,341  4/1970  Elslager et al. ................ 424/273 H OTHER PUBLICATIONS
Chemical Abstracts, 71: 124442f (1969).

Primary Examiner—Jerome D. Goldberg
Attorney, Agent, or Firm—Jerry F. Janssen

[57] ABSTRACT

The title compositions containing N,N-diethyl-5-methyl-2H-12-benzothiopyrano-4,3,2-cd-indazole-2-ethanamine as the free base (I) or pharmaceutically acceptable acid addition salt, and methods for their use are provided. The compositions are useful for treating tumors in warm blooded animals.

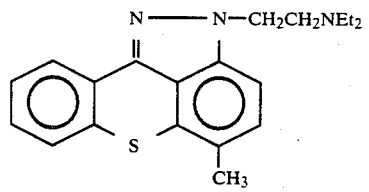

2 Claims, No Drawings

N,N-DIETHYL-5-METHYL-2H-1-BENZOTHI-OPYRANO-4,3,2-CD-INDAZOLE-2-ETHANAMINE COMPOSITIONS AND METHODS FOR THEIR USE

DESCRIPTION

1. Technical Field

This invention is directed to compositions containing N,N-diethyl-5-methyl-2H-1-benzothiopyrano-4,3,2-cd-indazole-2-ethanamine and to methods for their use. The compositions are useful for treating tumors in lower warm blooded animals.

2. Background of the Invention

The chemical compounds described as 5-methyl, hydroxymethyl, or 5-formyl benzothiopyranoindazole compounds, including N,N-diethyl-5-methyl-2H-1-benzothiopyrano-4,3,2-cd-indazole-2-ethanamine, and their use as antiparasitic and antibacterial agents, are known from U.S. Pat. No. 3,505,341.

SUMMARY AND DETAILED DESCRIPTION

The present invention is based on the unexpected finding that N,N-diethyl-5-methyl-2H-1-benzothiopyrano-4,3,2-cd-indazole-2-ethanamine, sometimes referred to hereinafter as Compound I, uniquely possesses outstanding antitumor properties. The invention therefore relates to pharmaceutical compositions for the treatment and inhibition of malignant tumors in lower warm blooded animals, containing as active ingredient an effective amount of Compound I in free base form or pharmaceutically acceptable salt form, and a pharmaceutically acceptable carrier.

Pharmaceutical compositions of the invention can take any of a wide variety of parenteral dosage forms. The dosage forms may comprise, as the active component, Compound I as the free base and/or corresponding pharmaceutically acceptable salt or salts, such a sulfate, phosphate or methanesulfonate salt. Other appropriate pharmaceutically acceptable salts within the scope of the invention are those derived from mineral acids such as hydrochloric acid and sulfamic acid; and organic acids such as ethanesulfonic acid, benzenesulfonic acid, p-toluenesulfonic acid and the like, giving the hydrochloride, sulfamate, ethanesulfonate, isethionate, benzenesulfonate, p-toluenesulfonate, lactate, gluconate, citrate, glucuronate, and the like. A preferred salt for purposes of the invention is the methanesulfonate.

The acid addition salts are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

For preparing pharmaceutical compositions, one uses inert, pharmaceutically acceptable carriers that can be either solid or liquid. Solid form preparations include ointments and suppositories. A solid carrier can be one or more substances which may also act as diluents, lubricants, suspending agents, or binders. Suitable solid carriers are polyethylene glycol, low melting wax, cocoa butter, and the like.

Liquid form preparations include solutions, suspensions, and emulsions. As an example may be mentioned water or water-propylene glycol solutions for parenteral injection. Liquid preparations can also be formulated in solution in aqueous polyethylene glycol solution.

Preferably, the pharmaceutical preparation is in unit dosage form. In such form, the preparation is subdivided into unit doses containing appropriate quantities of the active component. The unit dosage form can be a packaged preparation, for example vials or ampoules. The package containing discrete quantities of preparation.

The quantity of active compound in a unit dose of liquid preparation may be varied or adjusted from about 0.1 mg to about 500 mg according to the particular application and the potency of the active ingredient; from about 10 to about 100 mg/ml. of carrier is preferred. The daily parenteral doses for lower warm blooded animal subjects to be treated ranges from about 0.1 mg./kg. to about 100 mg./kg. The preferred daily dosage range is 1.0 mg./kg. to 10 mg./kg.

The pharmaceutical compositions, as indicated, are constituted so that they can be administered parenterally. Solutions of the active compound as a free base of pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The invention in another aspect concerns a method of inhibiting malignant tumors in lower warm blooded animals comprising administering to said lower warm blooded animals an effective amount of a pharmaceutical composition containing as active component at least about 0.1 percent by weight, based on the total weight of the composition, of N,N-diethyl-5-methyl-2H-1-benzothiopyrano-4,3,2-cd-indazole-2-ethanamine in free base form or a pharmaceutically acceptable salt form.

It is especially advantageous to formulate parenteral compositions in dosage unit form for ease of administration and uniformity of dosage. Dosage unit form as used herein refers to physically discrete units suitable as unitary dosages for the lower warm blooded animal subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitation inherent in the art of compounding such an active material.

The principal active ingredient is compounded for convenient and effective administration in effective amounts with a suitable pharmaceutically-acceptable carrier in dosage unit form as hereinbefore disclosed.

The usefulness of the pharmaceutical compositions of the present invention is demonstrated by the effectiveness of Compound I in standard laboratory animal antitumor activity test procedures, both in vivo and in vitro.

Test for In Vivo Antileukemic Activity

The in vivo lymphocytic leukemia P388 test is carried out by the United States National Cancer Institute. The animals used are either male or female $CD_2F_1$ mice. There are six to seven animals per test group. The tumor transplant is by intraperitoneal injection of dilute ascitic fluid containing cells of lymphocytic leukemia P388. The test compounds are administered intraperitoneally in two single doses with a four-day interval between doses at various dose levels following tumor inoculation. The animals are weighed and survivors are recorded on a regular basis for 30 days. A ratio of survival time for treated (T)/control (C) animals is calculated. The criterion for efficacy is $T/C \times 100 > 125\%$. The positive control compound in this test is 1,4-dihydroxy-5,8-[bis[[2-[(2-hydroxyethyl)amino]-ethyl]amino]-9,10-anthracenedione] given at dosages ranging from 12.0 to 0.075 mg/kg. See Cancer Chemotherapy Reports, Part 3, 3, 1 (1972) for a comprehensive discussion of the protocol.

Utilizing this procedure, the following results were obtained.

TABLE 1

| COMPOUND I, METHANESULFONATE (MTS) | |
|---|---|
| Dose mg/kg | T/C × 100 |
| 25 | 188; 215 |
| 12.5 | 136; 157 |

TABLE 2

Broad Spectrum Antitumor Activity* of COMPOUND I MTS·

| Tumor | Route Tumor/ Drug | Regimen | Dose mg/kg | T/C × 100 (Percent) | |
|---|---|---|---|---|---|
| B16 Melanoma (B6C3F1) | IP/IP | Q01D × 09 | 6.25 | 135 | |
| Colon 38** (BDF1) | SC/IP | Q07D × 02 | 100 50 | 16 37 | (One Cure) |
| Mammary** CD8F1 | SC/IP | Q07D × 05 | 100 50 | 20 13 | |
| Lewis Lung (BDF1) | IV/IP | Q01D × 09 | 25 | 156 | (3/10 Cures) |

*Procedure described in Cancer Chemotherapy Reviews, 7, 167 (1980) and references cited therein.
**For these tumors median tumor weight is evaluated versus controls rather than median survival time and T/C is the percentage of the tumor weight in the treated animals relative to the controls.

Test for In Vitro Activity Against Human Solid Tumors

HCT-8 (human colon adenocarcinoma) cells are trypsinized using Trypsin-EDTA. A single cell suspension is achieved by passing the cells through a 26 gauge needle with a 20 cc syringe. A cell suspension is prepared using RPMI 1640 + 10% FCS + 50 ug/ml garamycin with a cell concentration of approximately 30,000 cells/ml. The cell suspension is dispensed in Linbro 24-well plates; 1 ml/well. The plates are incubated for approximately 48 hours at 37 degrees C. in a 5% $CO_2$ atmosphere. At this time test compounds are added in the appropriate concentration. Five ul of the 200 ug/ml stock solution is added to each well in a primary test. Ten ul of the appropriate dilution is added to each well for a titration test. The plates are reincubated an additional 60–65 hours at 37 degrees C. in a 5% $CO_2$ atmosphere. The test is read by lysing the cells using a mix of cationic surfactant, glacial acetic acid and sodium chloride. Two ml of the lysed cell suspension from each well is added to 8 ml of diluent. Each sample is read on the Coulter counter (ZBI model). The activity of each sample is measured as a percentage of the controls and the data is reported as $ID_{50}$, that is the molar quantity of drug required to kill 50% of the tumor cells.

Utilizing this procedure, the result for Compound I methanesulfonate is $ID_{50} = 1.1 \times 10^{-6} M$.

PHARMACEUTICAL COMPOSITIONS

The following representative Examples are given as illustrative pharmaceutical compositions utilizing different carriers. In these examples, Example 1 illustrates the use of the compounds of the invention in injectables suitable for intravenous or other types of injection. Example 2 is directed to use of the compounds of the invention in suitable suppositories. For the Examples the content of Compound I is given as that of free base, and the ingredients are listed followed by the methods of preparing the compositions.

EXAMPLE 1

INJECTABLES

Example 1a COMPOUND I, hydrochloride salt

| | |
|---|---|
| COMPOUND I | 125 mg–500 mg |
| Water for Injection USP q.s. | |

COMPOUND I is dissolved in the water and passed through a 0.22 micron filter. The filtered solution is added to ampoules or vials, sealed and sterilized.

Example 1b COMPOUND I, methanesulfonate salt

| | |
|---|---|
| COMPOUND I | 125 mg–500 mg |
| Water for Injection USP q.s. | |

Prepared as per Example 1a above.

EXAMPLE 2

SUPPOSITORIES

Example 2a COMPOUND I, methanesulfonate salt 125 mg 250 mg or 500 mg per 3 g

| | | | |
|---|---|---|---|
| COMPOUND I | 125 mg | 250 mg | 500 mg |
| 1540 Polyethylene Glycol | 1925 mg | 1750 mg | 1400 mg |
| 8000 Polyethylene Glycol | 825 mg | 750 mg | 600 mg |

Melt the Polyethylene Glycol 1540 and the Polyethylene Glycol 8000 together at 60 degrees C. and dissolve COMPOUND I into the melt. Mold this total at 25 degrees C. into appropriate suppositories.

Example 2b COMPOUND I, hydrochloride salt 125, 250, 500 mg per 3 g

| | | | |
|---|---|---|---|
| COMPOUND I | 125 mg | 200 mg | 500 mg |
| 1540 Polyethylene Glycol | 1925 mg | 1750 mg | 1400 mg |
| 8000 Polyethylene Glycol | 825 mg | 750 mg | 600 mg |

Prepare as per Example 2a above.

Having described the invention, the embodiments of the invention in which an exclusive property or privilege is claimed are defined as follows:

1. A method of treating lower warm blooded animal tumors comprising: administering to a lower warm blooded animal in need of such treatment a tumor inhibiting amount of a pharmaceutical composition containing as active component N,N-diethyl-5-methyl-2H-1-benzothiopyrano(4,3,2-cd)indazole-2-ethanamine in free base form or a pharmaceutically acceptable salt form.

2. A method according to claim 1 where the active ingredient is in the methanesulfonate salt form.

* * * * *